United States Patent [19]

Mele

[11] Patent Number: 4,928,712
[45] Date of Patent: May 29, 1990

[54] INTRAVENOUS BOARDS

[76] Inventor: William D. Mele, 65 Park Terrace, Mill Valley, Calif. 94941

[21] Appl. No.: 277,650

[22] Filed: Nov. 29, 1988

[51] Int. Cl.⁵ ............................................. A61M 5/00
[52] U.S. Cl. .................................... 128/877; 128/878
[58] Field of Search ............... 128/846, 869, 877, 878, 128/879

[56] References Cited

U.S. PATENT DOCUMENTS

| | | | |
|---|---|---|---|
| 613,334 | 11/1888 | Thompson | 128/875 |
| 1,048,033 | 12/1912 | Brown | 128/875 |
| 3,059,636 | 10/1962 | Schwartz | 128/877 |
| 3,556,092 | 1/1971 | Eisenberg | 128/877 |
| 3,590,817 | 7/1971 | Wresch | 128/877 |
| 3,640,273 | 2/1972 | Ray | 128/877 |
| 4,286,588 | 9/1981 | Lovegrove | 128/877 |
| 4,290,425 | 9/1981 | Helfer et al. | 128/877 |
| 4,369,774 | 1/1983 | Robbins | 128/877 |
| 4,425,913 | 1/1984 | Lewis | 128/877 |
| 4,449,975 | 5/1984 | Perry | 128/877 X |
| 4,457,754 | 7/1984 | Buttaravoli | 128/877 X |
| 4,470,410 | 9/1984 | Elliott | 128/877 |
| 4,678,462 | 7/1987 | Vaillancourt | 128/877 X |

*Primary Examiner*—Robert A. Hafer
*Assistant Examiner*—Kevin G. Rooney
*Attorney, Agent, or Firm*—Douglas E. White

[57] ABSTRACT

An intravenous tube attachment board has a padded base about which are encircled two straps of hook and loop material such as that sold under the trademark VELCRO. The hook and loop material is modified by adding an inner adhesive layer covered with a paper strip and a plastic flap. By removing the paper strips, the IV tube may be firmly grasped between the adhesive layers and the flaps when the straps are used to hold a patient's arm or hand to the base of the board.

10 Claims, 3 Drawing Sheets

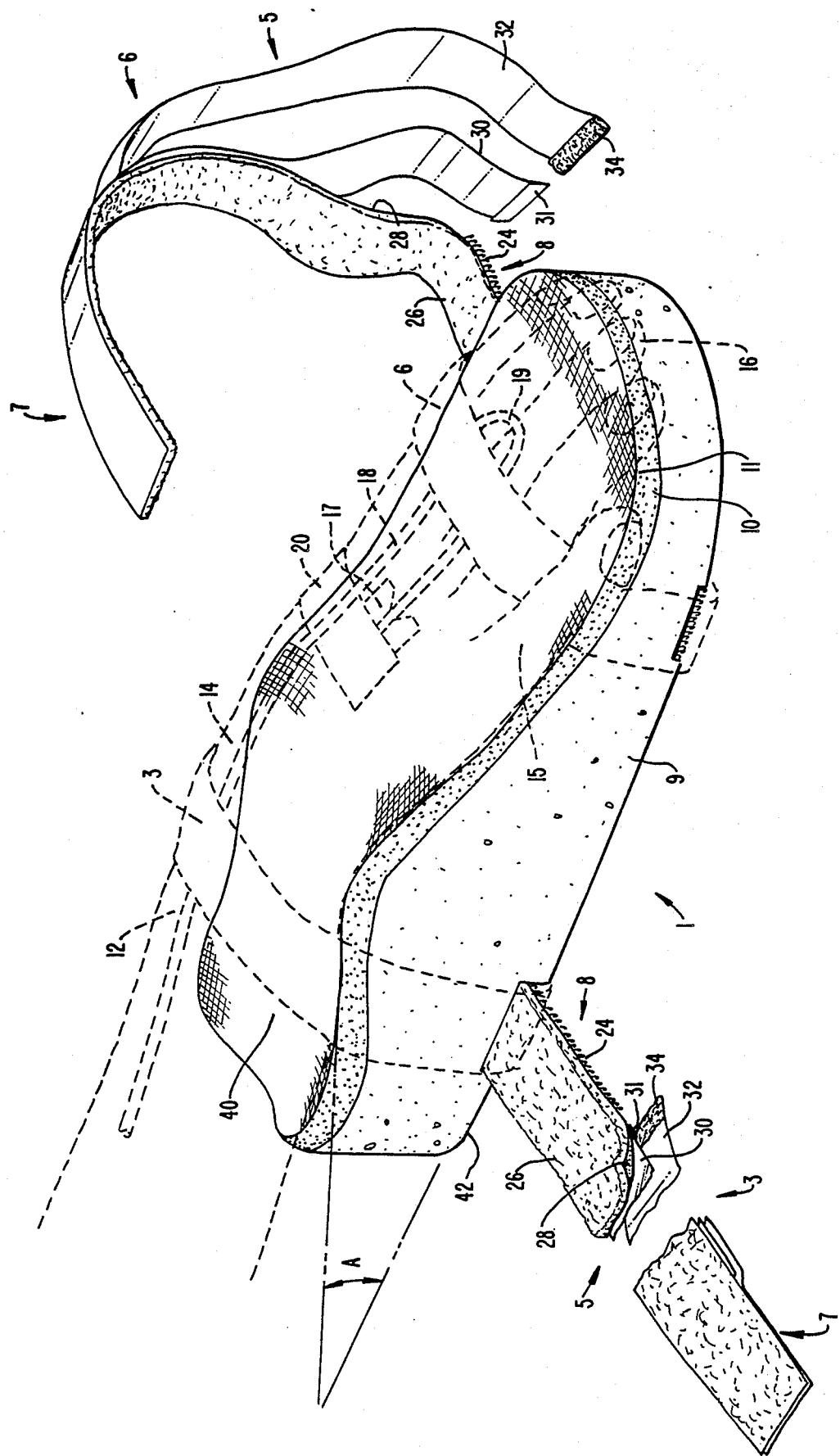
FIG._1.

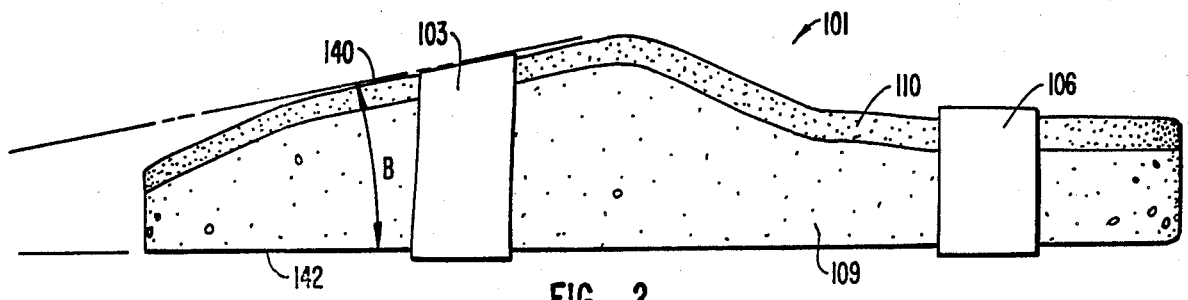
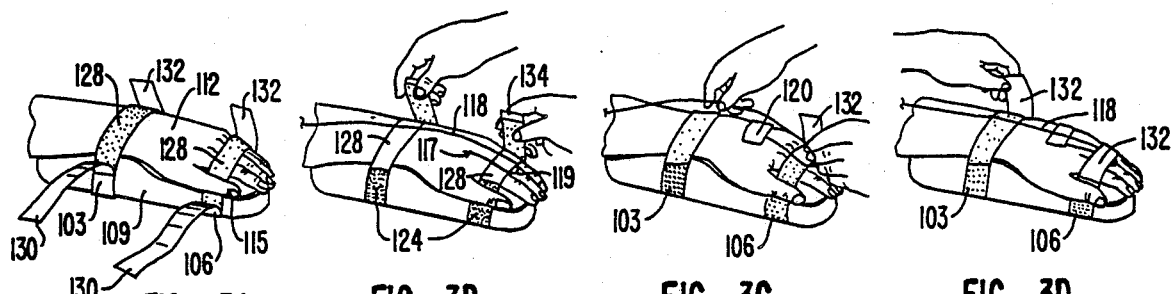
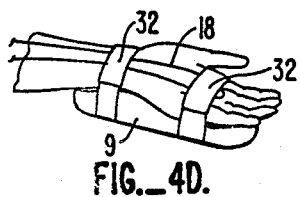
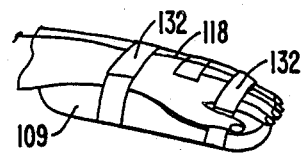
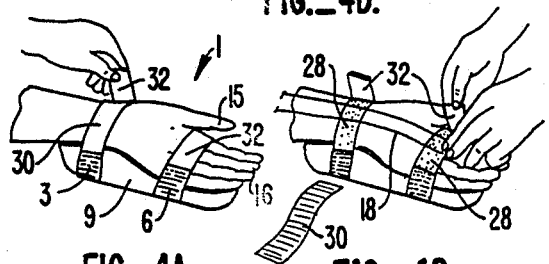
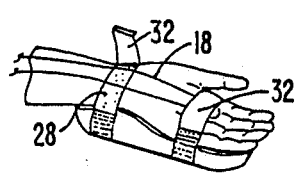
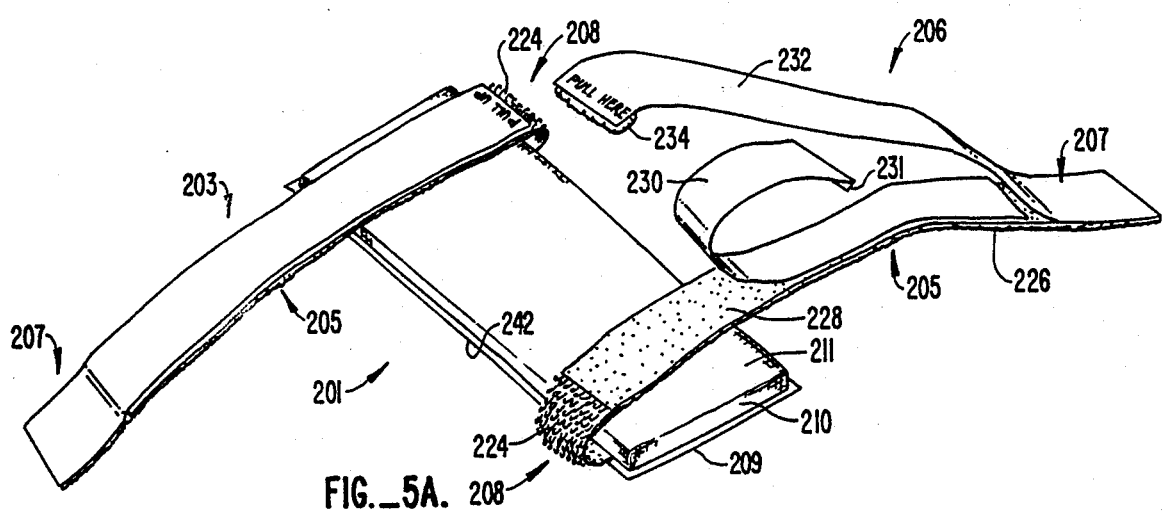

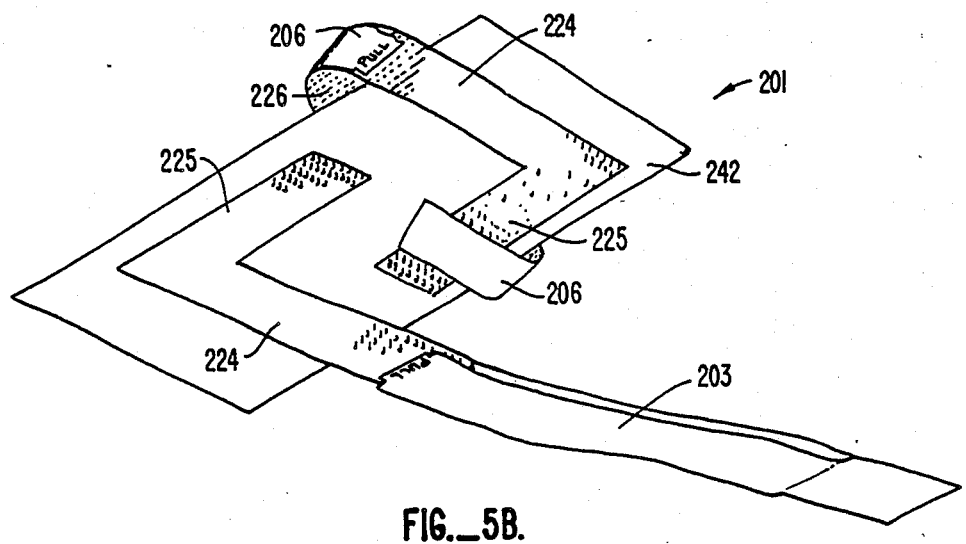
FIG._5B.
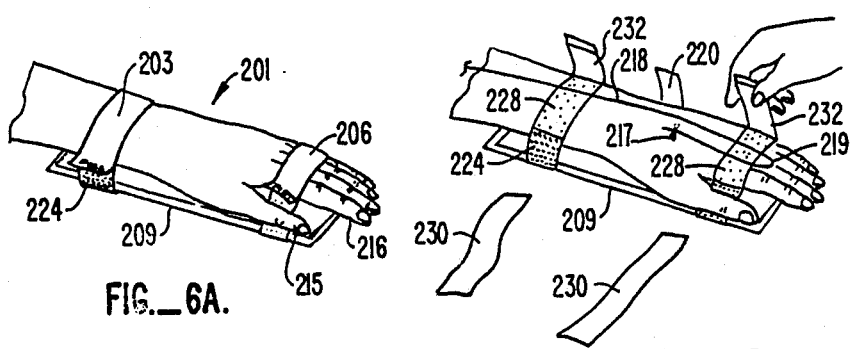
FIG._6A.  FIG._6B.
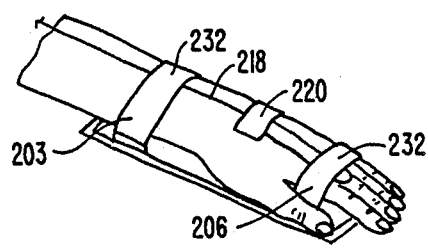
FIG._6C.
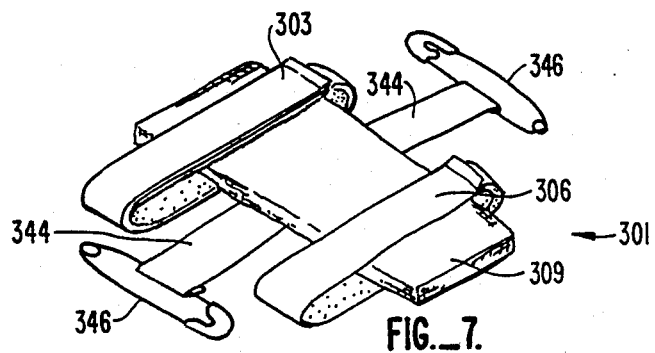
FIG._7.

INTRAVENOUS BOARDS

FIELD OF THE INVENTION

This invention relates to intravenous (IV) equipment for use in surgical and general medical treatment, more particularly to IV boards for immobilizing patient's hands and for supporting and securing IV butterflies and IV tubes.

BACKGROUND OF THE INVENTION

Both during surgery and afterward, it is common to administer fluids containing drugs and/or nourishment to a patient through a tube inserted into a vein in a lower arm or the back of a hand of the patient. While blood or a similar replacement fluid may be administered through an artery, both methods are commonly referred to as intravenous or "IV" procedures. The IV tube originates at a fluid reservoir and terminates at a butterfly mechanism. The butterfly leads to a hollow needle which punctures the vein (or artery) and establishes fluid communication between the vein, the IV tube and the associated fluid reservoir.

It is necessary, particularly in the case of drugged, sleeping, comatose, or infant patients, to strictly limit the movement of the arm or hand relative to the IV equipment in order that the latter not become disconnected inadvertently. Presently, this is accomplished by taping the hand to a flat, rigid board. Several full wraps of tape first are applied to the wrist and a separate wrapping is applied over the fingers. This holds the hand to the board. The IV then is inserted, for example, into a vein in the back of the hand. At this point, the wrapping of tape over the existing wrappings is resumed so that the IV tube becomes sandwiched between layers of tape. The hand then is not able to flex (because of the board) and the IV tube is not able to move with respect to the hand (because of the tape.) This immobilizes the IV butterfly within the area between the wrist and the fingers.

This is a clumsy, time-consuming and inexact procedure, due to the necessity of passing a tape spool over and under the patient's hand or arm and around a board a number of times. When the IV is removed, the tape must be cut away. The portion contacting the patient's skin may adhere strongly and cause discomfort upon removal.

It is often desirable to tilt the hand at the wrist at an angle with respect to the arm. In surgical applications, where the butterfly may be inserted in an artery in the lower arm, the desired angle becomes relatively steep. To achieve these angles, it is common to insert toweling between the wrist and the board, a procedure which is inexact, at best. Furthermore, this creates additional septic materials which later must be re-sterilized.

Accordingly, it is desired to introduce new apparatus for immobilizing IV implants which is easy to install and remove, is completely self-contained and disposable, and is cost-effective to produce.

SUMMARY OF THE INVENTION

The present invention is a padded intravenous board which uses a specially modified form of interlocking hook and loop material, such as that sold in unmodified form under the trademark VELCRO, to immobilize the patient's hand or arm and to secure IV equipment in place thereon.

Straps of hook and loop material of fixed length replace the multiple windings of tape characteristic of the art. A portion of each strap has an inner layer of adhesive material which is in the nature of normal tape adhesive. This adhesive is covered by a removable paper strip which temporarily separates the adhesive from a plastic flap. By removing the paper and inserting the IV tubing against the adhesive, one can secure the tubing between the strap and the flap.

In addition to flat IV boards, IV boards are disclosed which have bases molded of expanded polystyrene plastic foam, such as that commonly sold under the trademark STYROFOAM, so as to incorporate the exact wrist bend needed for the procedure being performed.

FEATURES AND ADVANTAGES

An object of this invention is to eliminate the unwieldy taping maneuver required to immobilize the limb in the present art. Accordingly, straps of hook and loop material are attached to the boards of my invention which are of lengths fixed to accommodate a range of limb sizes without having to encircle the limb more than once.

Another object is to eliminate the further circumferential taping used to affix the IV tubing to the top of the tape which first immobilized the limb. Accordingly, the hook and loop straps have upper inner adhesive layers and plastic flaps between which the tubing quickly may be sandwiched without encircling maneuvers.

A further feature is the provision of removeable paper strips which temporarily separate the plastic flaps from the adhesive of the straps, rendering the flaps easy to open in the first instance and difficult to open after the paper strips are removed.

Another feature is a small tab of loop material which holds the plastic flap temporarily in place over the paper strip, protecting the adhesive layer prior to use.

Yet another object is to eliminate the need to pad the patient's wrist with towels or the like in order to flex it at a desired angle. Accordingly, some of my boards have a molded raised portion which establishes a precise angle of flex. Furthermore, the board's base may be molded to fit the natural contours of the hand, greatly increasing patient comfort over long periods of use.

Yet another object is to disclose a foam padding for the base which further increases comfort and also aids circulation.

A further object is to disclose a "L" shaped leg of hook material on the bottom of the base which allows the loop material to be affixed in a hurry without the need for precise emplacement.

Yet another feature or object is to provide a board with wing bands terminating in safety pins for use, in the case of infants, in affixing the board to bedding.

Yet a further object is to disclose boards of various sizes, shapes and number of straps, for use in a wide variety of applications.

Other novel features which are characteristic of the invention, as to organization and method of operation, together with further objects and advantages thereof will be better understood from the following description considered in connection with the accompanying drawing in which a preferred embodiment of the invention is illustrated by way of example. It is to be expressly understood, however, that the drawing is for the purpose of illustration and description only and is not intended as a definition of the limits of the invention.

Certain terminology and derivations thereof may be used in the following description for convenience in reference only and will not be limiting. For example, the words "upwardly," "downwardly," "leftwardly," and "rightwardly" will refer to directions in the drawings to which reference is made. The words "inwardly" and "outwardly" will refer to directions toward and away from, respectively, the geometric center of a device and designated parts thereof.

BRIEF DESCRIPTION OF THE DRAWING

FIG. 1 is a perspective view of a thirty degree IV arterial board of the present invention;

FIG. 2 is a frontal elevation of a five degree IV arm board;

FIGS. 3A–3E illustrate, in a series of views advancing with respect to time, the method of installing the arm board of FIG. 2;

FIGS. 4A–4D illustrate, in a series of views advancing with respect to time, the method of installing the arterial board of FIG. 1;

FIGS. 5A and 5B are two perspective views of a IV hand board, taken from the top and the bottom thereof, respectively;

FIGS. 6A–6C illustrate, in a series of views advancing with respect to time, the method of installing the hand board of FIG. 5; and FIG. 7 is a perspective view of an IV infant board.

DRAWING REFERENCE NUMERALS

A 30 degree angle
1 30 degree arterial board
3 wrist strap
5 mid-portion of 3,6
6 finger strap
7 outer end of 3,6
8 inner end of 3,6
9 base
10 pad, foam
11 fabric
12 hand
14 wrist
15 thumb
16 fingers
17 IV butterfly
18 IV tube
19 loop in 18
20 tape
24 hook material
26 loop material
28 adhesive layer
30 paper strip, removeable
31 tab
32 plastic flap
34 loop material tab
40 cylindrical section, concave
42 bottom plane of 9
B 5 degree angle
101 5 degree arm board
103 wrist strap
106 finger strap
109 base
110 pad, foam
112 hand
117 IV butterfly
118 IV tube
119 loop in 118
120 tape
124 hook material
128 adhesive layer
130 paper strip, removeable
132 plastic flap
140 cylindrical section, concave
142 bottom plane of 109
201 IV hand board
203 wrist strap
205 mid-portion of 203,206
206 finger strap
207 outer end of 203,206
208 inner end of 203,206
209 base
210 pad, foam
211 fabric
215 thumb
216 fingers
217 IV butterfly
218 IV tube
219 loop in 218
220 tape
224 hook material
225 L-shaped inner legs of 203,206
226 loop material
228 adhesive layer
230 paper strip, removeable
231 tab
232 plastic flap
234 loop material tab
242 bottom plane of 209
301 infant IV board
303 wrist strap
306 finger strap
309 base
344 wing bands
346 safety pins of 344

DESCRIPTION OF A PREFERRED EMBODIMENT

Referring to FIG. 1, there is illustrated therein a preferred IV arterial board 1, showing its installation on a patient's hand 12 (the latter shown in phantom). While the hand 12 is shown in FIG. 1 with its palm down, in order best to illustrate emplacement of a IV butterfly 17, it is to be understood that all of the boards illustrated in the drawing may be used either palm down or palm up, as desired. In fact, the board of FIG. 1 normally will be installed palm up, as shown in FIG. 4, for reasons discussed below.

Arterial board 1 has a wrist strap 3 (shown broken to fit within the drawing) toward its rear and a finger strap 6 toward its front. Straps 3,6 are attached at their inner ends 8 to the bottom 42 of the rigid polystyrene foam base 9 of the board. The base has a layer of foam padding 10 which is covered with a smooth fabric 11 on its upper surface for the comfort of the patient and for the maintenance of blood circulation.

The straps 3,6 are of sufficient length to completely encircle the base and overlap upon themselves, as shown in phantom in FIG. 1, even when a large hand is encountered. While it is preferred that the straps encircle the base in opposite directions, as shown, for example, in FIGS. 1 and 5, they can just as easily be mounted to turn in the same direction, as shown in FIGS. 3, 4, 6 and 7.

While the roles of hook material and of loop material as discussed herein could be reversed, the inner end 8 of each strap preferably is covered with VELCRO-type hook material 24 on the side of the strap facing outwardly with respect to the base 9.

A strongly adhering adhesive layer 28 extends the full length of each strap and is used, among other things, to affix the strap to the base at end 8. At the outer end 7 of each strap the adhesive is used to secure a plastic flap 32 in place. The side of the strap facing inwardly toward the base preferably is formed of loop material 26 from the point of attachment of the hook material 24 onto the base, to the outer end 7 of the strap.

Between ends 7,8 there is a mid-portion 5 whose length is preferably greater than that of either of the end portions. This mid-portion is defined by a removeable strip of high-gloss paper 30 to which the adhesive will not readily adhere. This paper is used temporarily to separate the plastic flap 32 from the adhesive 28 throughout the mid-portion 5 until the board 1 is installed.

The paper 30 terminates at the end of the hook material 24 where the former is turned up to form a pull-tab 31. The plastic flap 32 extends a short distance beyond this, i.e. somewhat into the inner end 8, in order to overlap slightly the hook material 24. Flap 32 terminates on its inward end with a small tab of loop material 34 on its inner surface, which tab is used to hold the flap in place over the paper strip 30 prior to removal of the latter.

As shown in phantom in FIG. 1, an IV butterfly 17 is in fluid communication with an IV tube 18 that leads to a fluid reservoir (not illustrated). As in the prior art, the butterfly is secured to the back of the patient's hand 12 after insertion of the needle by means of a piece of tape 20, which tape may or may not be supplied as an integral part of the board. As will be discussed in detail below, a loop 19 in the tube 18 then is sandwiched securely in place between the adhesive 28 and the plastic flap 32 of finger strap 6. An additional portion of the tube 18 is also sandwiched between the adhesive and the flap of wrist strap 3.

The upper surface of the base 9 is smoothly rounded to fit the natural contours of the hand. The rear of the base thus has a concave portion 40 shaped roughly like a section of a cylinder corresponding to the convex cylindrical shape of a patient's lower arm. The imaginary axis of the cylindrical section 40 meets the plane of the bottom 42 of the base at a thirty degree angle A in a preferred arterial board 1.

Turning to FIG. 4 and referring back to FIG. 1 as necessary, the method of installing the arterial board 1 will be discussed. It will be recalled that the preferred installation of the board 1, as opposed to that of most other boards, is with the patient's palm upward. In this fashion, angle A causes the wrist to bend or cock to the extent specified in many surgical procedures. The point of attachment of the butterfly 17, when the palm is turned up, is to an artery of the arm (the latter of which is out of view in FIG. 4.)

With the straps 3,6 unfurled, the patient's hand 12 is placed on the board and the straps are wound over upon themselves to a point where the loop material 26 engages the hook material 24 and secures the hand to the base 9. The wrist strap 3 encircles the patient's wrist 14. The finger strap 6 encircles the patient's fingers 16, but, for comfort, does not have to trap the thumb 15.

The plastic flaps 32 are then pulled back one at a time, as shown in FIG. 4A. In FIG. 4B the paper strips 30 are removed and discarded. The IV tube 18 is looped to reverse its direction of travel and is pressed in place on top of the adhesive layers 28 at the points where it crosses the two straps. The plastic flaps 32 are then placed back in position on top of the adhesive one at a time, as seen in FIGS. 4C and 4D. However, with the removal of the paper strips, the flaps are very securely held in place and no longer may easily be removed. Therefore, the IV tube 18 is as much secured as it is under the current method wherein it is held in place by multiple windings of tape.

A five degree intravenous arm board 101 and its method of use are illustrated in FIGS. 2 and 3. It is to be noted for convenient reference that the last two positions of the reference numerals of FIGS. 2, 3, and 5-7 duplicate those of the reference numerals of FIG. 1 when they refer to corresponding parts.

The five degree board 101 also has at least two straps, a wrist strap 103 and a finger strap 106, attached to a molded STYROFOAM base 109. The top of base 109 is covered with foam rubber or other suitable padding 110. The only significant difference between boards 1 and 101 is that the latter is somewhat longer and that angle B, between the axis of the concave partially cylindrically shaped portion 140 of board 101 and the plane of the bottom 142 of its base, is about five degrees. This angle produces the bend of the wrist desired for insertion of the IV butterfly 117 into a vein of the back of the hand when the patient's palm is facing downward, which is the preferred hand attitude for IV board 101.

With the straps 103,106 unfurled, the patient's hand is placed on the board and the straps are wound over upon themselves to a point where the loop material engages the hook material 124 and secures the hand to the base 109. The wrist strap 103 encircles the patient's wrist. The finger strap 106 encircles the patient's fingers, but does not have to trap the thumb.

The plastic flaps 132 are then pulled back one at a time and the paper strips 130 removed and discarded, as shown in FIGS. 3A and 3B. The butterfly 117 is inserted into a vein of the back of the hand and held in place with tape 120 as seen in FIG. 3C. The loop 119 of IV tube 118 is pressed in place on top of the adhesive layer 128 of the finger strap 106. The tube 118 is also pressed in place on top of the adhesive layer of the wrist strap 103 at the point where the tube crosses the strap. The plastic flaps 32 are then placed back in position this time directly on top of their respective adhesive layers 128 as seen in FIGS. 3D and 3E.

FIG. 5 illustrates another embodiment of the invention, namely a flat hand board 201. Board 201 may be constructed of a thin sheet of plywood, plastic or other rigid planar material and covered with padding 210 and fabric 211. Flat base 209 has at least two modified interlocking hook and loop material straps 203,206 as previously discussed. In the case of long boards (not illustrated), there may be three or more arm, wrist and finger straps.

Plastic flaps 232 are secured to the outer ends 207 of the straps 203,206 by an adhesive layer 228 and have loop material tabs 234 to secure their ends to the hook material 224 of the inner ends 208 of the straps. The flaps are temporarily prevented from adhering to the adhesive within the mid-portions 205 of the straps by paper strips 230, which strips are removed in use by pulling tabs 231. The inwardly directed side of the straps is formed of loop material 226.

The bottom 242 of the base 209 of the board 201 is shown in FIG. 5B. The hooked inner end portions 208 have L-shaped legs 225. These legs allow the straps to be looped around the base in an angled or off-center manner as shown in the case of strap 206. This feature is useful when attachment of the IV board 201 must be accomplished in a hurry or when an unusual configuration of IV apparatus is encountered. Boards 1,101 will also have such legs, but they are not visible in the drawing.

FIG. 6A shows a patient's hand after the straps 203,206 have been wound and secured by interlocking hook 224 and loop 226 material. FIG. 6B shows removal of the paper strips 230, the attachment of the butterfly 217 with tape 220, and the attachment of the IV tube 218 against adhesive layers 228. FIG. 6C shows the completion of installation where the plastic flaps 232 have been replaced directly on top of the adhesive, as discussed in detail above in connection with other boards.

Finally, FIG. 7 shows yet another embodiment of the invention - in this case, a flat infant's IV board 301. Parts 303, 306, and 309 are constructed and function as previously discussed in connection with other boards. However, since infants may not be cautioned to keep their hands and arms steady, a pair of wing bands 344 are added. The bands terminate in safety pins 346. The pins 346 are used to secure the board to the infant patient's bedding or bedclothes. This provides added protection against dislodging the IV apparatus.

While the above provides a full and complete disclosure of the preferred embodiments of this invention, various modifications, alternate constructions, and equivalents may be employed without departing from the true spirit and scope of the invention. Therefore, the above description and illustrations should not be construed as limiting the scope of the invention which is defined by the appended claims.

I claim:

1. A board for attaching an intravenous tube to a patient including:
   a rigid base forming an arm board;
   at least two straps affixed to the base by a first layer of strongly adhering adhesive, the straps having interlocking hook and loop material for securing the straps about the base;
   a second layer of tape adhesive material on a surface of each strap for attaching the tube to the straps;
   a plastic flap covering the second tape adhesive layer of each strap;
   loop material on one end of each of the plastic flaps;
   a removeable paper strip between the second tape adhesive layer and the flap;
   a bottom surface of the base; and
   an L-shaped leg on at least one strap on the bottom surface of the base.

2. A board for attaching an intravenous tube to a patient including:
   a rigid padded base having front and rear ends and a central portion which is raised with respect to the two ends;
   a planar bottom surface of the base;
   a curvilinear upper surface of the base;
   a hand rest section of the upper surface at the front end of the base;
   a generally concave partially cylindrical arm rest section of the upper surface at the rear end of the base, the arm rest section having an axis
   wherein the axis of the arm rest section intersects the plane of the bottom at an acute angle and the arm rest section joins the hand rest section at the raised central portion;
   at least two straps each having interlocking hook and loop material for securing the straps about the base, the straps affixed and strongly adhering to the base at an inner strap end of each strap;
   a layer of tape adhesive material on a surface of each strap for attaching the tube to the strap;
   a plastic flap covering the tape adhesive layer of each strap;
   interlocking hook and loop material on an outer flap end of each of the plastic flaps; and
   a removeable paper strip between each tape adhesive layer and the flap.

3. The apparatus of claim 2 further including:
   an L-shaped leg on at least one strap on the bottom surface of the base.

4. The apparatus of claim 2 wherein:
   the base is made of polystyrene foam and the angle is thirty degrees.

5. The apparatus of claim 2 wherein:
   the base is made of polystyrene foam and the angle is five degrees.

6. A board for attaching an intravenous tube to a patient including:
   a rigid padded base having a bottom surface;
   a plurality of straps, each strap affixed at a first fixed strap end to the bottom surface by a strongly adhering base adhesive, each strap having
      a first surface having loop material on a second free strap end,
      a second surface having hook material on the first fixed strap end;
   a layer of strap tape adhesive material on the first surface of at least one strap;
   a plastic flap covering the strap adhesive layer, the flap terminating in a tab of loop material for engaging with the hook material on the first fixed strap end;
   a removeable glossy paper strip between the adhesive layer and the flap; and
   an L-shaped leg covered with hook material on at least one strap on the bottom surface of the base.

7. The apparatus of claim 6 further including:
   a pair of wing bands extending from the base, each band having pin means for securing the bands.

8. The apparatus of claim 7 wherein:
   there are two straps and each strap has a layer of strap adhesive material.

9. The apparatus of claim 1 further including:
   a pair of wing bands extending from the base, each band having pin means for securing the bands.

10. The apparatus of claim 2 further including:
    a pair of wing bands extending from the base, each band having pin means for securing the bands.

* * * * *